United States Patent [19]

De Fraites

[11] 4,316,871
[45] Feb. 23, 1982

[54] REFUSE DISINFECTION DEVICE

[76] Inventor: Emanuel G. De Fraites, 535 Iris Ave., New Orleans, La. 70121

[21] Appl. No.: 175,846

[22] Filed: Aug. 7, 1980

[51] Int. Cl.³ ............................................. A61L 2/06
[52] U.S. Cl. ...................................... 422/26; 422/295
[58] Field of Search ................... 422/26, 27, 28, 29, 422/32, 295, 297, 292

[56] References Cited

U.S. PATENT DOCUMENTS 2,731,208  1/1956  Dodd ............................. 422/295 X
4,088,444  5/1978  Byrne .................................. 422/25

FOREIGN PATENT DOCUMENTS 2160434  6/1973  Fed. Rep. of Germany ........ 422/26

*Primary Examiner*—Barry Richman
*Attorney, Agent, or Firm*—Thomas S. Keaty; Gregory C. Smith; George A. Bode

[57] ABSTRACT

A method and apparatus for the steam disinfection of refuse, particularly garbage received, under quarantine, from marine vessels. The apparatus is a closable chamber having a steam sparger supported above the bottom thereof, which sparger is covered by water placed in the bottom of the chamber during use thereof.

2 Claims, 3 Drawing Figures

REFUSE DISINFECTION DEVICE

BACKGROUND OF THE INVENTION

1. Field of the Invention

The present invention relates to the disinfection of refuse such as garbage. The present invention more particularly relates to an apparatus for the disinfection of garbage and the like especially when received from marine vessels and under quarantine.

2. General Background and Prior Art

In the marine industry, it has been commonplace in past years for the garbage which accumulates on the ship and like refuse to be merely cast overboard during the journey into the surrounding ocean.

The dumping of such refuse or garbage at sea has now become illegal and seamen are required to dispose of their accumulated garbage at the port which is their destination.

In the United States, refuse, garbage and the like is quarantined by the Food and Drug Administration as soon as the garbage reaches the dock.

Inspectors from the Food and Drug Administration will normally require that the crewmen seal up the refuse or garbage in an approved container and, thereafter, demand that it be disposed of by suitable means to prevent the transfer of harmful disease or bacteria to the continental United States.

One prior art method for dealing with this problem has been the incineration or burning of the garbage which itself contributes to environmental pollution.

It would be desirable to have a method and apparatus for the disinfection of garbage, refuse and like materials accumulated on the ships which system for disinfection could quickly and easily rid the shipowner of the refuse problem.

Several prior art devices have been patented which attempt to disinfect or sterilize garbage, refuse or the like in some sort of container.

U.S. Pat. No. 4,017,980 issued to R. A. Kleinguenther, entitled "Apparatus and Process for Treating Wood and Fibrous Materials" teaches the use of an apparatus and process for treating wood and other fibrous materials within a hermetically sealed, heat insulated chamber at a certain atmospheric pressure and temperature range, the purpose of which would be to dry the fibrous materials to increase the tensile strength.

U.S. Pat. No. 1,955,289 issued to B. Greenfield, entitled "Steam Cooking Process" would teach the use for a method for cooking foods wherein the food may be cooked at various temperatures out of contact with the fuel gases and under a flowing pressure of a premixed stream of air and steam, by allowing the cooking chamber to have continuous ventilation to the atmosphere.

U.S. Pat. No. 4,160,445 issued to Paul Kunz, entitled "Pressure Vessel and Method for Cooking Food in a Pressure Vessel" would teach the use of a pressure vessel having therein a first zone in which solid material is introduced, and a second zone in the lower portion of the vessel where liquid is accumulated during the cooking process.

U.S. Pat. No. 3,721,527 issued to W. Lodige, et al, entitled "Method for Sterilizing Bulk Materials" teaches the use of sterilization by means of steam or hot gas, wherein batches of material are centrifuged in a closed chamber with simultaneous addition of sterilizing medium. Thereafter, the sterilizing medium is separated out from the material at a sub-atmospheric pressure with centrifuging of the material.

U.S. Pat. No. 1,902,625 issued to A. L. Dunham, entitled "Method and Apparatus for Sterilizing" teaches a method of sterilization by the use of superheated steam, in a closed chamber which is heated to a desired temperature by the introduction of the superheated steam at comparatively low pressure. The sterilization would take place in a dry atmosphere in order to maintain the temperature within the chamber above the point of steam condensation.

U.S. Pat. No. 4,050,388 issued to John A. Boyd, entitled "Refuse Treatment Apparatus" teaches the treatment of refuse by directing the non-pulverized refuse material into a furnace. A steam supply is introduced into the inlet end of the drum to admix with the refuse material being fed thereinto. The non-pulverized refuse material emerging from the outlet end of the drum would then pass through a series of treatment steps.

U.S. Pat. No. 2,260,710 issued to J. F. Gschwind entitled "Autoclave and the Like" would teach the use of an arrangement of direct and indirect heat sources in autoclaves to assure a quick heating up and a minimum of the heat and condensate losses. The invention would further prevent the loss of any heating fluids during the curing period inasmuch as there is no need for additional heating.

GENERAL DISCUSSION OF THE PRESENT INVENTION

The present invention solves these prior art problems and shortcoming by providing a disinfection device for use with garbage and refuse from shipowners which provides a spacious container having an inner refuse or garbage holding portion with movable lids which allow the addition of garbage or the like to the container and can thereafter be shut to seal the refuse inside. If desired, a plurality of lifting eyes can be located on the container which adapted for lifting onto the deck or into the hold of a ship where the garbage to be disinfected can be added to the container.

A continuous elongated steam sparger is provided on the inner portion of the container adjacent but spaced from the bottom. One end portion of the sparger outcrops the side wall portion of the container where a valve, for example, can be provided for valving the flow of steam to the inner portion of the container through the steam sparger.

In the preferred embodiment, the sparger comprises an elongated pipe having perforations which are spaced a desired distance and are patterned, for example, to spray steam downwardly toward the floor of the container at an angle with respect to the container floor. In the preferred embodiment, the sparger is formed by a plurality of generally parallel pipe sections which are joined at their end portions using, for example, elbow connections. Thus, a continuous elongated sparger is provided covering substantially an entire container floor and providing for substantially equal distribution of steam over the entire floor of the apparatus. During operation, water is preferably added to the container to a degree which fills the container with water to a level which submerges the entire steam coil sparger in water prior to the disinfection of garbage by the introduction of steam.

A garbage product to be added is added to the interior of the container with the sparger being spaced off the bottom of the container and with the openings being directed downwardly to prevent clogging.

Thus, it is an object of the present invention to provide a system for the disinfection of garbage which can be easily adapted for disinfection of garbage from ocean-going vessels, ships and the like.

It is another object of the present invention to provide a disinfection apparatus which disinfects garbage, refuse and the like using steam.

Another object of the present invention is to provide a garbage disinfection apparatus which quickly and easily disinfects garbage in relatively large quantities in a relatively short period of time.

It is another object of the present invention to provide an apparatus for the disinfection of garbage which is simple and easy to use.

It is another object of the present invention to provide an apparatus for the disinfection of garbage which is mobile, and can be easily transported from a vessel generating the garbage to an area where steam can be added to the apparatus and thence to a dump sight.

It is another object of the present invention to provide a garbage disinfection apparatus which can be easily sealed to safely contain quarantined garbage or the like which must thereafter be disinfected.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PREFERRED EMBODIMENT

Figure 1:
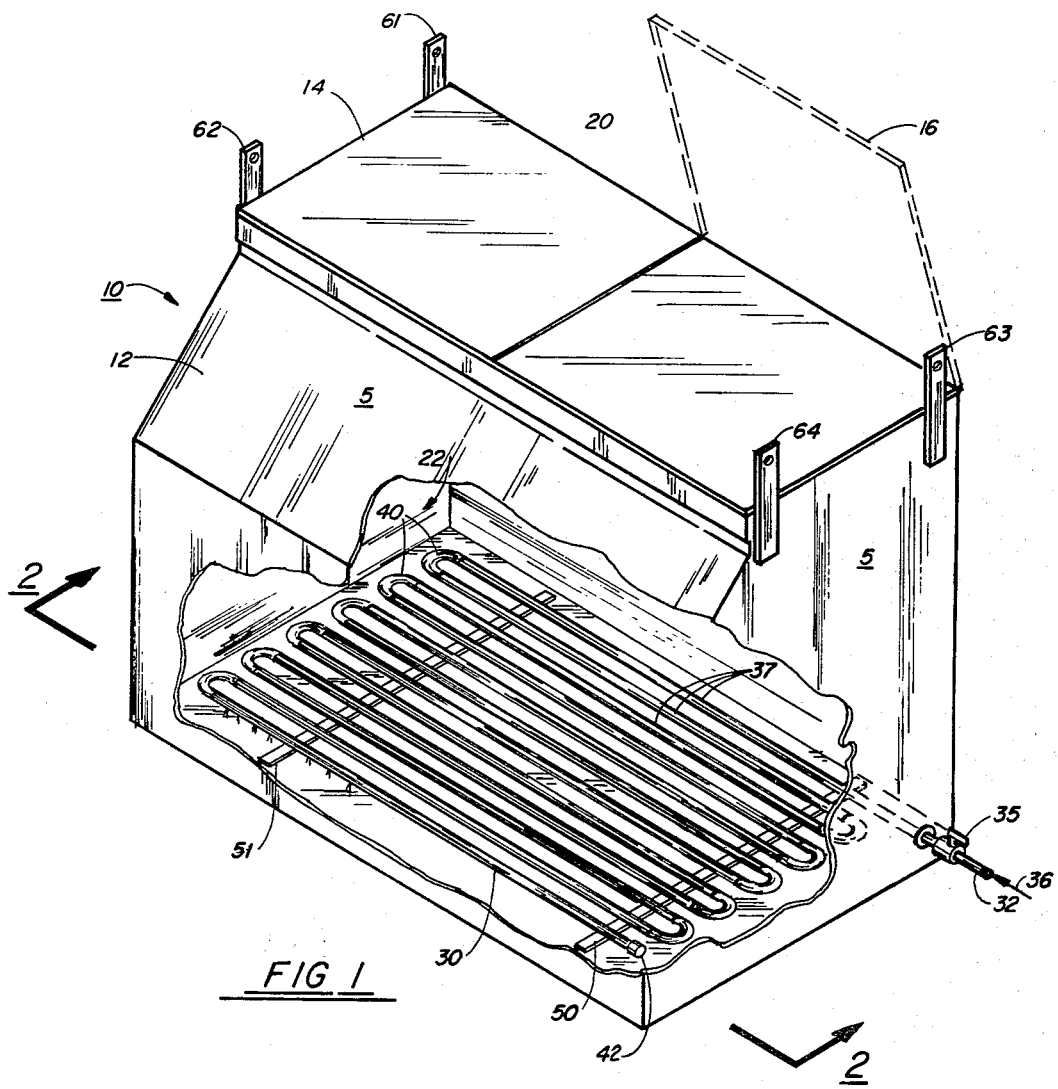
FIG. 1 is a perspective, partially cut away view of the preferred embodiment of the apparatus of the present invention.

FIG. 1 best illustrates the preferred embodiment of the apparatus of the present invention designated generally by the numeral 10. In FIG. 1, there can be seen a garbage disposal apparatus 10 which comprises generally a container 12 having lid portions 18, 16 attached hingedly thereto with the lids being movable in a pivotal fashion to open and close the provided upper opening 20 to container 12 which allows the entry of garbage, refuse or the like into the inner space 22 portion of container 12.

Container 12 provides within its inner space 22 and more specifically on the bottom portion thereof a continuous steam coil sparger 30 which sparger has an inlet 32 end portion provided with a valve 35 for controlling or valving the flow of steam into container 12 through sparger 30, the inflow of steam being schematically illustrated by the arrow 36 in FIG. 1.

Sparger 30 can be, for example, in the form of a plurality of substantially parallel pipe members 37 (12 being preferred) which are connected alternately at the end portions by elbow fittings 40.

The extreme end portion of sparger 30 from inlet 32 provides a cap 42. It will be understood by one skilled in the art, that the flow of steam from inlet 32 will be generally toward cap 42 with steam between inlet 32 and cap 42 leaving sparger 30 through provided openings 45 (see FIG. 3).

Figure 2:
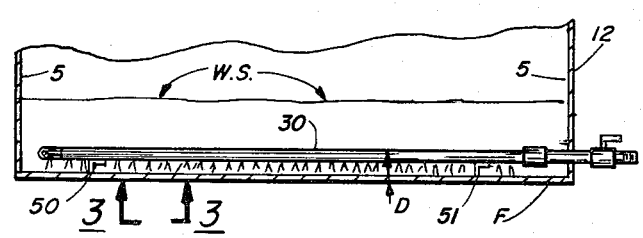
FIG. 2 is a sectional view taken along lines 2—2 of FIG. 1.

A pair of spacer support racks 50, 51 are seen best in FIGS. 1 and 2. Support racks 50, 51 are provided to space sparger 30 a distance D above the floor F of container 12 with a four to six inch spacing D being preferable.

Container 12 comprises generally a floor F portion and four sidewalls each being designated by the letter S.

Figure 3:
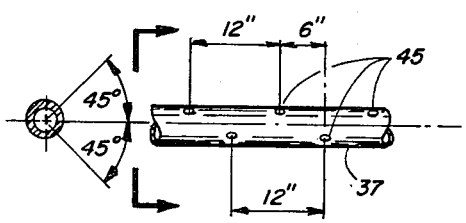
FIG. 3 is a bottom view of the steam coil sparger portion of the preferred embodiment of the apparatus of the present invention, which is also a sectional view taken along lines 3—3 of FIG. 2.

In FIG. 3, there is seen a detail of a single sparger pipe 37 with discharge openings 45 being shown thereon. Openings 45 could be, for example, equally spaced a distance of six inches apart with each consecutive opening 45 being placed at an orientation of forty-five degrees (45°) downwardly with respect to the horizontal while alternating in forwardly and rearwardly disposed positions. Thus, steam would be distributed to the left and to the right of each sparger pipe 37 to provide an even distribution of steam within the inner space 22 of container 12.

As schematically shown in FIG. 2, water would preferably be added to inner space 22 above floor F of container 12 to a level WS which would submerge sparger 30 minutes before the introduction of steam at inlet 32. This has been found to provide a method and apparatus for the quick and complete disinfection of any mass of garbage which is added to container 12 through opening 22.

A plurality of lifting eyes 61–64 can be provided for attaching container 12 to a crane or the like for elevating container 12 onto the deck of a vessel where a mass of garbage to be disinfected can be added thereto.

The container of the present invention thus provides an easily movable container apparatus 10 which can be lifted onto the vessel, with the garbage or refuse product thereafter added and the container sealed on the vessel by appropriate authorities.

Container 12 could be, for example, welded steel construction while sparger could be in the form of a continuous sparger comprised of a plurality of pipe sections, each being preferably of extra heavy thickness steel pipe or the like.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of disinfecting refuse products comprising:
    a. placement of refuse products into a container having an inner space and an upper opening for adding said refuse products to the inner space portion of said container, and an elongated steam coil sparger mounted in said container at the bottom portion thereof;
    b. closing a movable door portion for containing said refuse products in said container in a sealing fashion;
    c. injecting water into the said container to a level to cover the said elongated steam coil sparger;
    d. injecting steam into said elongated steam coil sparger;
    e. allowing said steam to flow out of said sparger through a plurality of equally spaced steam discharging openings provided in said sparger on the lower portion thereof, each of said openings facing downwardly, at least in part, and located alternately left and right of the line of the pipe sections;

f. steaming the refuse products for a time sufficient to allow disinfection to occur;

g. providing a pair of support members for spacing said sparger above the floor portion of said container.

2. The method for disinfecting refuse products in claim 1, wherein said sparger further comprises a plurality of elongated parallel pipe portions, with each consecutive pair of pipe sections being joined at one end portion allowing a continuous sparger through which steam can flow to all of the pipe sections.

* * * * *